United States Patent [19]

Laine et al.

[11] Patent Number: 5,216,155

[45] Date of Patent: Jun. 1, 1993

[54] SILICON AND ALUMINUM COMPLEXES

[75] Inventors: Richard M. Laine, Ann Arbor, Mich.; Kay A. Youngdahl, Issaquah, Wash.

[73] Assignee: Washington Research Foundation, Seattle, Wash.

[21] Appl. No.: 792,214

[22] Filed: Nov. 12, 1991

Related U.S. Application Data

[63] Continuation-in-part of Ser. No. 509,022, Apr. 13, 1990, Pat. No. 5,099,052.

[51] Int. Cl.$^5$ .............................. C07F 5/06; C07F 7/02
[52] U.S. Cl. .............................. 544/181; 544/225; 544/229; 546/2; 546/14; 549/210; 549/214; 556/9; 556/27; 556/173; 556/174; 556/175; 556/182; 556/405; 556/443; 556/464; 556/482
[58] Field of Search ............... 556/175, 182, 443, 464, 556/482, 9, 27, 405, 173, 174; 544/181, 225, 229; 546/2, 14; 549/210, 214

[56] References Cited

U.S. PATENT DOCUMENTS

| | | | |
|---|---|---|---|
| 3,455,980 | 7/1969 | Frye | 260/448.8 |
| 4,447,628 | 5/1984 | Farnham | 556/415 |
| 4,577,003 | 3/1986 | Farnham | 556/464 |
| 4,617,413 | 10/1986 | Corriu et al. | 556/464 |
| 4,632,967 | 12/1986 | Farnham | 526/194 |
| 4,841,084 | 6/1989 | Corriu et al. | 556/464 |
| 5,099,052 | 3/1992 | Laine | 556/443 |

OTHER PUBLICATIONS

Boudin et al., Angew. Chem. Int. Ed. Engl., vol. 25, No. 5, pp. 474–475 (1986).

Youndahl, K. A. and R. M. Laine, "Synthesis of Soluble Siliconates and Siloxanes from Silica" (abstract No. 421), Spring Newsletter, Jan. 1989, Division of Inorganic Chemistry, American Chemical Society.

Holmes, R. R. Et al., "Cyclic Pentaoxy Siliconates," Phosphorus, Sulfur, and Silicon, 1989, vol. 42, pp. 1–13.

Barnum D. W., "Reactions of Catechol with Colloidal Silica and Silicic Acid in Aqueous Ammonium", Inorganic Chemistry, vol. 11, No. 6, 1972.

Perozzi et al., J. Am. Chem. Soc., vol. 106, pp. 1591–1593, 1979.

Farnham et al., J. Am. Chem. Soc., vol. 103, pp. 4608–4610, 1981.

Frye, C. L., J. Am. Chem. Soc., vol. 92, No. 5, pp. 1205–1210, 1970.

Frye, C. L. et al., J. Am. Chem. Soc., vol. 93, No. 25, pp. 6805–6811, 1971.

Laine, R. M. et al., Nature, vol. 353, pp. 642–644, 1991.

Primary Examiner—Jose G. Dees
Assistant Examiner—Porfirio Nazario
Attorney, Agent, or Firm—Christensen, O'Connor, Johnson & Kindness

[57] ABSTRACT

Silicon and aluminum complexes having the following formula I, II or III:

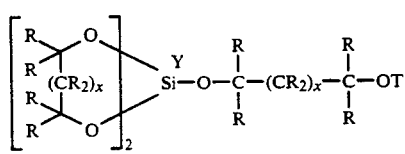

I

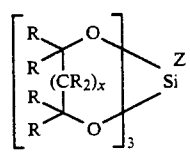

II

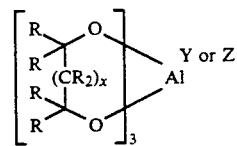

III wherein x is 0 or 1, T is H or (Abstract continued on next page.)

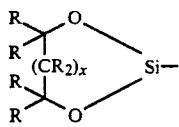

each R is independently selected from the group consisting of H, OH, $C_{1-6}$ alkyl, $C_{1-6}$ alkoxy, $C_{2-6}$ alkene, $C_{6-12}$ aryl, $C_{1-6}$ hydroxyalkyl, $C_{1-6}$ thioalkyl, $C_{2-12}$ alkoxyalkyl, $C_{3-20}$ heteroaromatic, and combinations thereof, wherein R may further contain one or more atoms of a non-carbon element such as Si, Ge, Sn, P, and the like; Y is a cation, and Z is a multivalent cation, are prepared by reacting silica or alumina with a diol, in the presence of a base, while removing water formed during the reaction. Methods for producing such complexes starting with silica or alumina, and methods for converting such complexes into other silicon or aluminum-containing compounds, are disclosed.

16 Claims, No Drawings

SILICON AND ALUMINUM COMPLEXES

The invention was made with government support under the following grants: N00014-88-K-0305 and F49620-89-C-0059. The government may have certain rights in this invention.

This application is a continuation-in-part of U.S. application Ser. No. 07/509,022, filed Apr. 13, 1990, now U.S. Pat. No. 5,099,052.

FIELD OF THE INVENTION

The present invention relates to complexes containing at least one silicon or aluminum atom, to the preparation of such complexes starting with silica or alumina (in various chemical and mineral forms), and to the use of these complexes to prepare other silicon or aluminum-containing compounds.

BACKGROUND OF THE INVENTION

Silicon-based chemicals are used in a wide variety of applications, such as in biocides, stain- and dirt-resistant polymers for carpets, advanced ceramics for aerospace applications and electronic components. The market for silica and other silicon-containing materials amounts to several billion dollars per year. One important aspect of this market, not immediately evident even to a first-hand observer, is the fact that all silicon-based materials beyond sand are produced by primitive ceramics processing technologies that: (1) add considerable cost to the typical product; (2) limit the scope of applications, and (3) offer limited opportunity for growth because of the maturity of the process.

Silicon products may be derived from the carbothermal reduction of silica to silicon metal:

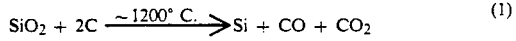

The resulting metallurgical grade silicon (90–98% purity) must then undergo further processing to make other products. For example, to make many of the industrially useful (high purity) forms of silica (e.g., fumed or electronics grade silica), it is necessary to first react the Si metal produced in reaction (1) with $Cl_2$ or HCl to make $SiCl_4$ which can then be burned (e.g., reaction 4):

$$Si + 2Cl_2 \rightarrow SiCl_4 \qquad (2)$$

$$Si + HCl \rightarrow HSiCl_3 + SiCl_4 \qquad (3)$$

$$SiCl_4 + H_2O + O_2 \rightarrow SiO_2 + HCl + HClO_x \qquad (4)$$

Carbothermal reduction requires high heat and specialized equipment. The result is an energy and equipment intensive process. Reaction of silicon with chlorine or HCl also requires specialized, expensive equipment to deal with toxic and corrosive materials. Despite these considerable drawbacks, because the basic technology was developed late in the last century and early in this century, all of the processing problems have been worked out. This, coupled with economies of scale, makes this approach to the production of fumed and electronics grade silica commercially successful.

Similar problems pervade the alumina and aluminum chemicals technologies. Indeed, these technologies are even more expensive and complex because of the need to electrolytically reduce molten alumina/cryolite melts to form aluminum, the source of most aluminum chemicals and many aluminum containing ceramics.

The production of silicon-based chemicals follows somewhat similar chemistry. Most silicone polymers derive from the "Direct Process":

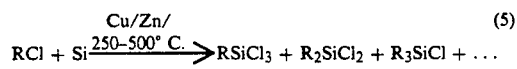

This simple reaction only works well when RCl is MeCl or PhCl. When it is MeCl, the major product is $Me_2SiCl_2$, which is hydrolyzed and polymerized to give polydimethylsiloxane, the basic silicone polymer:

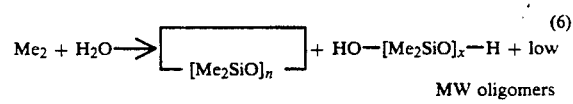

wherein n is 3–5 and x<100

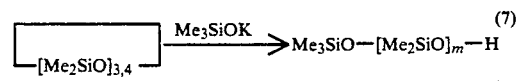

The above reactions, when coupled with standard organic chemistry reactions, some special derivatives and processing procedures, provide the basis for the major portion of the silicone and silicon chemicals industry. It is surprising that there are few, if any, alternate methods for producing silicon-based polymers. If there were, and these new methods provided commercially competitive materials even a fraction as successful as the silicone polymers, the rewards would be exceptional. Preferably, these new methods should also involve an inexpensive and readily available starting material. In view of this, silica is an attractive starting material for producing silicon-containing species, such as those described above.

Silica, $SiO_2$, is the most common material found in nature. As sand, it is a basic ingredient in building materials, the manufacture of low-tech glass products and ceramics. In purer forms, it is used as an abrasive (e.g., toothpaste) and as a drying and texturizing agent in food-related products. It is also used in the manufacture of electronic materials and optical products.

Silica is also a feedstock material used for the manufacture of silicon-based chemicals. Synthetic routes stemming from the use of silica gel offer the important attribute of being very inexpensive (research grade silica sells for ~$15/kg or less). Additionally, silica gel is very easy to handle due to its relative nonreactivity. Industrial fused silica sells for less than $1/kg, and can be used here.

On the other hand, because of its low reactivity, there are few simple, low-temperature methods of chemically modifying silica. One such method is dissolution in base to give sodium silicate:

$$NaOH + SiO_2 \rightarrow Na_4SiO_4 \qquad (8)$$

Unfortunately, this reaction has limited application for the formation of useful feedstock chemicals. The recent work of Kenny and Goodwin [*Inorganic and Organometallic Polymers*, N. Zeldin et al., ACS Symposium Series 360, 238 (1987)] on silicic acid esterification provides one successful transformation:

(9)

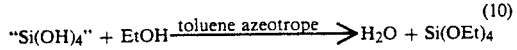

(10)

Si(OEt)$_4$, currently produced by reaction of EtOH with SiCl$_4$, reaction (11), is used commercially to form fumed and electronics grade silica.

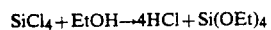

(11)

It is also used to form optical glasses and boules for spinning fiber optics.

It has been reported that soluble complexes of silicon can be prepared from silica gel and catechol in water. These reports teach that the reactions of silica with 1,2 aromatic diols lead to the formation of hexacoordinate, monomeric silicon complexes:

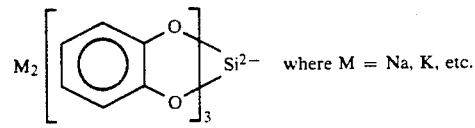

This approach was modified and refined by Corriu and co-workers by using basic methanol solutions under anhydrous conditions. A. Boudin, et. al., *Angew. Chem. Int. Ed. Engl*, 25 (5):474–475 (1986). These stable salts could then be alkylated by strong nucleophiles, such as Grignard reagents, to form three (and frequently four) new silicon-carbon bonds:

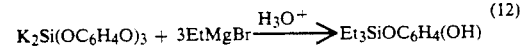

(12)

The problem with this approach is that the catechol complex, tris(1,2-dihydroxobenzoato) siliconate, is relatively expensive and can only be modified under forcing conditions using expensive reagents such as LiAlH$_4$, RMgBr, or RLi and the products are limited to tri- or tetrasubstituted silicon. Consequently, its large scale utility is limited. Furthermore, formation of mono- and dialkyl derivatives was not possible.

The invention described herein resulted from an exploration into methods of making more reactive complexes of silica using aliphatic 1,2- or 1,3-diols, such as ethylene glycol, instead of catechol. Thus, one aspect of the present invention, described in greater detail hereinbelow, involves certain novel silicon complexes that may be formed by a reaction between silica and 1,2- or 1,3-aliphatic diols. These complexes have been determined to contain one or more anionic pentacoordinate silicon atoms when a monovalent counterion is involved and to contain an anionic hexacoordinate silicon atom when divalent or higher valency counterions are involved.

Previously, pentacoordinate silicon species have been reported. For example, U.S. Pat. No. 3,455,980 discloses pentacoordinate silicon complexes of vicinal aliphatic diols, including ethylene glycol. The disclosure in this patent differs from the present invention, however, in that these prior complexes were not formed from silica but, rather, from a compound of the formula (R'O)$_4$Si in the presence of excess aliphatic diol and an amine. Also, the structures of the pentacoordinate silicon species disclosed in this patent are different from the structures of those disclosed herein.

U.S. Pat. Nos. 4,632,967, 4,577,033, and 4,447,628 are also directed to penta-coordinate silicates, all of which have structures that are different from those of the present invention.

Generally, the prior art has taught that only monomeric, pentacoordinate silicon complexes derive from monomeric tetracoordinate silicon complexes and only dimeric complexes from dimeric starting materials (always bridged by polyalkyl siloxanes). This is despite forming monomeric pentacoordinate silicon under conditions where sufficient diol is added to form dimeric species.

In an article entitled "Pentacoordinate Silicon Derivatives. IV.1 Alkylammonium Siliconate Salts Derived from Aliphatic 1,2-Diols" [C. L. Frye, *J. Am. Chem. Soc.* 92(5):1204–1210 (1970)], there are disclosed silicon-based compounds that are similar to, but structurally different from, those of the present invention.

Some additional publications that may be relevant to the background of the present invention are the following: "Cyclic Pentaoxy Siliconates," R. R. Holmes et al., *Phosphorus, Sulfur and Silicon and the Related Elements* 42:1–13 (1989); "Reaction of Grignard Reagents With Dianionic Hexacoordinated Silicon Complexes: Organosilicon Compounds from Silica Gel," A. Boudin, et. al., *Angew. Chem. Int. Ed. Engl,* 25(5):474–475 (1986); "Reaction of Catechol with Colloidal Silica and Silicic Acid in Aqueous Ammonia," D. W. Barnum, *Inorganic Chemistry* 11(6):1424–1429 (1972); and "Pentacoordinate Silicon Compounds. V.1a Novel Silatrane Chemistry," C. L. Frye, et al., *J. Am. Chem. Soc.* 93(25):6805–6811 (1971).

In spite of previous work involving functionalization of silica and other work involving preparation of pentacoordinate and hexacoordinate silicon complexes, there has remained a need for new and improved ways of producing useful silicon compounds. The present invention provides novel penta-coordinate silicon complexes, methods of preparing them from silica, and process for converting silica into a variety of useful silicon compounds via these complexes.

In a similar fashion, it has been found that alumina (Al$_2$O$_3$) can also be converted to soluble chemical complexes by reaction with base in the presence of diols.

SUMMARY OF THE INVENTION

An object of the present invention is to enable preparation of useful silicon-containing compounds using silica as a starting material.

It is another object of the present invention to obtain silicon-containing compounds that may be further reacted to produce a variety of useful silicon compounds.

It is yet another object of the present invention to provide a method for making soluble silicon products starting with silica and using simple and inexpensive reactions.

It is yet another object of the invention to demonstrate that this approach can be applied to another metal oxide, alumina.

The above and other objects of the present invention, as will hereinafter become more readily apparent, have been achieved by the discovery that silica or alumina can be made to react with aliphatic diols in the presence of a base and with removal of water during the reaction, to produce pentacoordinate or hexacoordinate silicon complexes, or tetra-, penta- or hexacoordinate aluminum complexes. These complexes may be relatively easily functionalized by way of further chemical reactions to produce a variety of valuable silicon and aluminum containing compounds. Through purification and hydrolysis, these compounds can be used directly to form high purity silica or alumina. Alternatively, when heated they can serve as precursors to a wide variety of glasses and ceramics.

The initial product of the reaction between the aliphatic glycol and silica or alumina may also be transformed into other products by way of ligand exchange reactions employing different ligands or cation exchange reactions employing different cations.

In general, the reactions of the present invention to produce silicon or aluminum complexes may be depicted as shown in the following scheme:

Y is monovalent cationic, and Z is multivalent cationic, preferably dicationic.

The product of the above reaction is a monomeric (T=H) or dimeric (T=other than H) silicon complex or an aluminum complex. As noted above, the product may subsequently be reacted with another ligand or another cationic species to result in a ligand or cation exchanged product. The product of the above reaction may also be converted into other useful silicon or aluminum-containing compounds or ceramics, e.g., via standard methodologies.

DETAILED DESCRIPTION OF THE INVENTION

The present invention is based on a discovery that silica or alumina can be converted into silicon or aluminum complexes under relatively mild reaction condi-

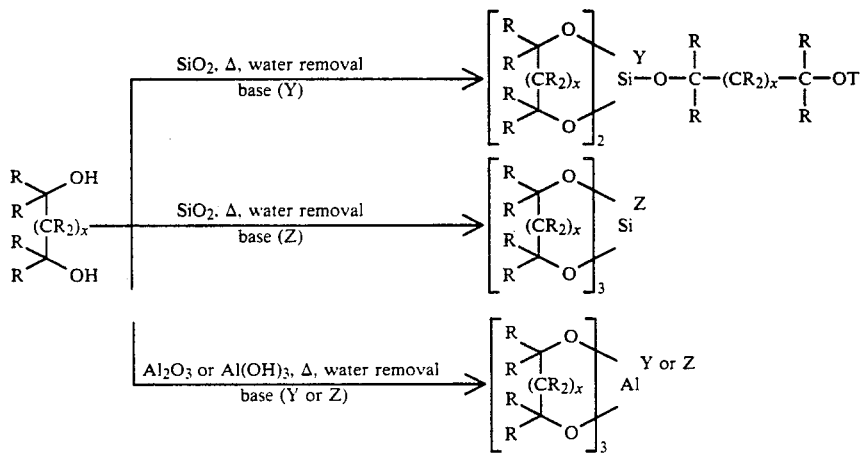

wherein x is 0 or 1, each R is independently selected from H, OH, $C_{1-6}$ alkyl, O- $C_{1-6}$ alkyl, $C_{2-6}$ alkene, $C_{6-12}$ aryl, $C_{1-6}$ hydroxyalkyl, $C_{1-6}$ thioalkyl, $C_{2-12}$ alkoxyalkyl, $C_{3-20}$ heteroaromatic, and combinations thereof, wherein the R groups may also contain other, non-carbon elements such as Si, Sn, Ge, P, and the like; T is H or

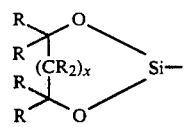

tions by causing the silica or alumina to react with an aliphatic diol in the presence of a bse, while removing water that is formed during the reaction. The reaction produces silicon complexes or aluminum complexes, often in high yield.

The following scheme depicts an exemplary reaction starting with silica to form a complex of the present invention in the presence of the monovalent cation $K^+$, and several secondary reactions that lead to a variety of useful silicon-containing products:

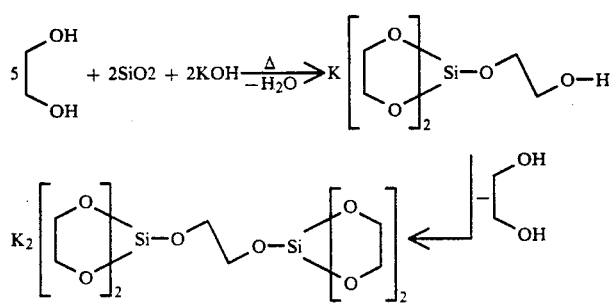

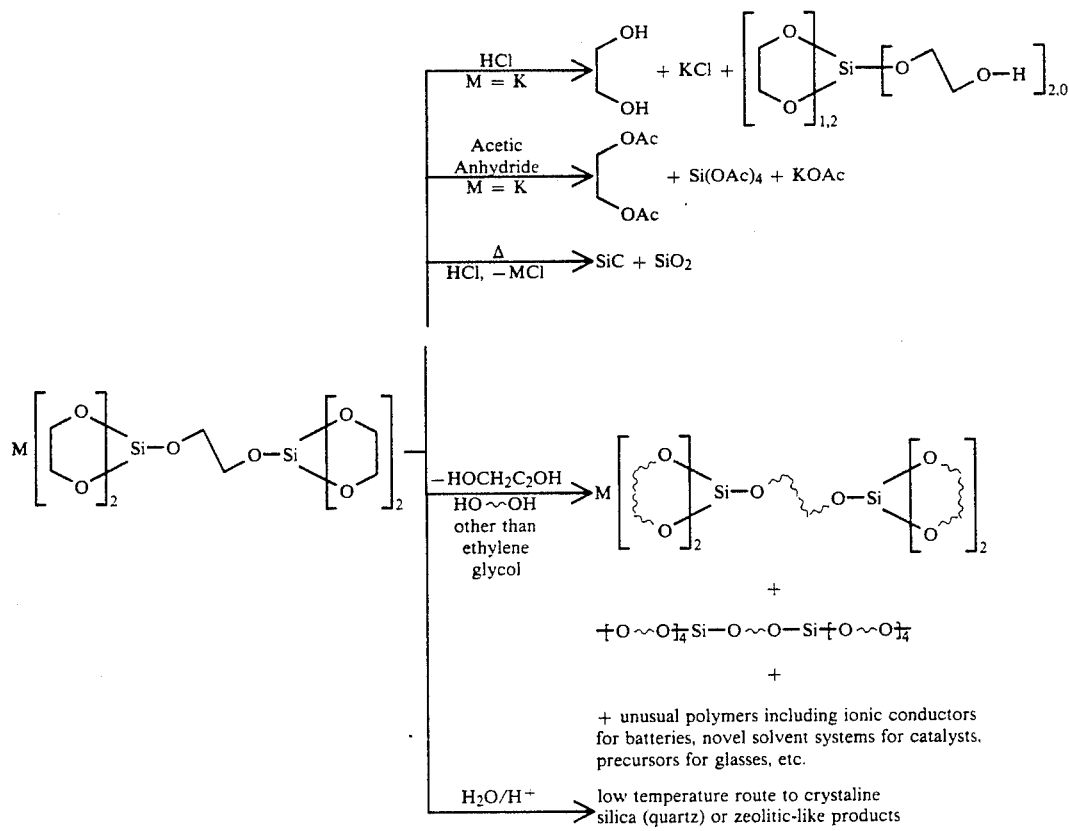

The following scheme depicts an exemplary reaction starting with silica to form a complex of the present invention in the presence of the divalent cation Ba$^{++}$:

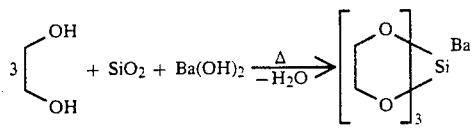

The starting materials, an aliphatic glycol, silica or alumina, and a base, may be obtained from commercial sources, such as the Sigma Chemical Company and the Aldrich Chemical Company, or may be synthesized using available starting materials and known reactions.

Generally speaking, a molar excess of an aliphatic diol is added to silica, alumina, or aluminum hydroxide and a base, a suitable solvent is added, and the mixture is allowed to react. It is possible to run the reaction in excess reactant as solvent. The molar ratio of diol:-silica:base is typically 3-5:1-3:1-3 and of diol:alumina:-base it is typically 3-7:1-3:1-9.

The base used in the reaction may be an alkali metal hydroxide or oxide, such as lithium hydroxide, sodium hydroxide, potassium hydroxide, or cesium hydroxide, an alkaline earth metal hydroxide or oxide, such as barium hydroxide, magnesium hydroxide, calcium hydroxide, barium oxide, magnesium oxide, calcium oxide, and the like. Surprisingly, when the counterion is monocationic, a mixture of monomeric and dimeric pentacoordinate silicon species is produced, whereas when the counterion is dicationic (e.g., Mg$^{2+}$, Ca$^{2+}$, Ba$^{2+}$, Sr$^{2+}$, Ni$^{2+}$, or Co$^{2+}$), a monomeric hexacoordinate species is produced. Tricationic or higher valent cationic species may also produce hexacoordinate species. When aluminum-containing reactants are employed, the products are tetracoordinate, pentacoordinate or hexacoordinate, such as, for example, KAl(OCH$_2$CH$_2$O)$_2$, Ba$_2$Al$_2$(OCH$_2$CH$_2$O)$_5$, and K$_3$Al(OCH$_2$CH$_2$O)$_3$, respectively. The base will generally provide the cation, Y or Z, in the final product.

As far as the inventors are aware, there are no specific requirements to be imposed on the cation, and a chemist will readily be able to select any of a variety of cations that will work for purposes of the present invention. However, many transition metal cations will be reduced if conditions are not suitable and care in choice of reaction conditions should be exercised with this in mind. It is preferred that the cation be derived from an alkali metal or alkaline earth metal, but it may also be derived from other chemical species.

An example of another chemical species that may serve as a cation in the silicon complexes is a quaternary salt. Suitable quaternary salts have the general structure:

R'$_4$EX wherein E is N, P, or Sb; each R' is independently C$_{1-4}$ alkyl, and X is an anion such as hydroxide or some species that generates OH$^-$ on reaction with water. Exemplary divalent cations are: Mg$^{2+}$, Ca$^{2+}$, Ba$^{2+}$, Sr$^{2+}$, Ni$^{2+}$, and Co$^{2+}$. The diol that is employed may be any one having the formula:

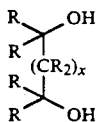

wherein x is 0 or 1, and each R is independently selected from H, OH, $C_{1-6}$ alkyl, $C_{1-6}$ alkoxy, $C_{2-6}$ alkene, $C_{6-12}$ aryl, $C_{1-6}$ hydroxyalkyl, $C_{1-6}$ thioalkyl, $C_{2-12}$ alkoxyalkyl, $C_{3-20}$ heteroaromatic, and combinations thereof, wherein R may have one or more (preferably 1–3) noncarbon elements, such as Si, Sn, Ge, and P.

The alkyl moieties may be straight chain, branched, and/or cyclic. Exemplary nonlimiting alkyl moieties are: methyl, ethyl, propyl, i-propyl, cyclopentyl, 2-methylbutyl, and the like.

The alkene moieties may be straight chain, branched and/or cyclic. Nonlimiting examples are the mono, di, and polyunsaturated analogues (where possible) of the above-listed alkyl groups having greater than two carbon atoms.

The aryl groups are generally aromatic hydrocarbon moieties that have 6 to 12 carbon atoms. The aryl groups may be attached directly to the diol or be attached by way of an intervening alkyl moiety. Nonlimiting examples of the aryl group are: benzyl, phenyl, and the like.

The hydroxyalkyl groups may be any straight chain, branched, and/or cyclic $C_{1-6}$ alkyl group substituted with one or more (preferably 1–3) hydroxyl groups. Nonlimiting examples are 1-hydroxyethyl, 2-hydroxyethyl, 1-hydroxypropyl, and the like.

The thioalkyl groups may be any straight chain, branched, and/or cyclic $C_{1-6}$ alkyl attached to the diol by way of a sulfur atom. Nonlimiting examples are any of the alkyl moieties described above attached by a sulfur atom to the diol.

The alkoxyalkyl groups may be any ether moiety containing 2 to 12 carbon atoms. Nonlimiting examples are methoxymethyl, ethoxymethyl, methoxyethyl, and the like.

The heteroaromatic groups may be any $C_{3-20}$ group (preferably $C_{3-8}$) containing one or more (preferably 1 or 2) heteroatoms (preferably O, N, and/or S). Nonlimiting examples are groups derived from pyridine, thiophene, pyrazine, triazine, etc.

Preferably, the diol is unsubstituted or is independently substituted by 1–3 nonhydrogen substituents. Also, the preferred substituents are $C_{1-6}$ alkyl or $C_{2-6}$ alkenyl. Further, the substituents are preferably located on different carbon atoms of the complex.

Some combinations of substituents will not be desirable due to incompatibility, steric crowding, and/or instability under reaction condition. One of ordinary skill will be able to determine these combinations based on standard synthetic considerations and/or routine experimentation.

Optically active diols are also contemplated; these diols may be resolved before use in the reaction, or may be used as a mixture of racemates. Similarly, the final products formed by using a diol with an optically active carbon atom may be resolved during purification or may be used as a mixture of stereoisomers.

Vicinal diols are preferred as the diols herein. However, under some circumstances, the hydroxyl groups may have a 1, 3 orientation on the diol, depending upon the flexibility of the diol ligand, etc.

Any grade or form of silica may be employed in the reactions. A preferred silica is 10–400 mesh with minimal organic impurities. However, even beach sand can be used.

Any grade or form of alumina or aluminum hydroxide may be used in the reaction. A preferred alumina is 10–400 mesh.

The basic reaction starting with silica or alumina that is described above may be conducted in a variety of solvents. Preferred solvents are higher boiling alcohols such as ethylene glycol, 2-aminoethanol, amyl alcohol, 2-ethoxyethanol, and the like. However, other solvents are also possible, such as DMSO, sulfolane, N-methyl pyrrolidone.

The reaction will generally be conducted at from ambient temperature to higher temperatures. Conveniently, the reaction may be conducted at the boiling point of the solvent that is employed. For most purposes, the upper limit of the temperature range will be approximately 200° C. Preferably, the temperature range will be from about 30°–170° C. Most preferably, the temperature will range from about 80° C. to 150° C.

It is important that substantially all water that is formed during the reaction be removed as it is formed. It has been found that if the water is not removed, the products described herein are not obtained. Conveniently, the water may be removed by azeotropic distillation; the precise temperature at which water can be azeotropically removed will depend upon the solvents which are used and other conditions, as will be readily understood by a synthetic chemist. The water may also be removed by known water-scavenging species or by any standard membrane transport protocol.

The reaction will typically be carried out for a time period of from a few minutes (e.g., twenty minutes) up to 2–4 days, as necessary.

The final product will often separate out of the reaction mixture as a precipitate on cooling; however, it may also remain dissolved in the reaction mixture and must be precipitated by addition of a nonsolvent such as acetonitrile. The product may be isolated and purified by any of a variety of standard methodologies. For example, the product may be taken up in a solvent, filtered, concentrated, and then crystallized. The crystallized product may then be recrystallized from a suitable solvent system. In some situations, it may be necessary to carry out column chromatography or another purification procedure to aid in the purification of the desired product.

In a preferred embodiment, ethylene glycol is reacted with silica in the presence of an alkali metal hydroxide or oxide to produce a dimeric pentacoordinate silicon complex, as depicted below:

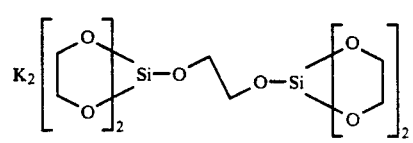

Other preferred reactants, etc., are summarized in the following Table:

| Diol | Base | Solvent | Reaction Temp. (°C.) | Product |
| --- | --- | --- | --- | --- |
| 1,2-ethanediol | MOH<br>M = Li, Na, K, Cs | $HOCH_2CH_2OH$ | 100–200 | $K_2Si_2(OCH_2CH_2O)_5$ |
| 1,2-ethanediol | $M(OH)_2$<br>M = Mg, Ca, Sr, Ba | $HOCH_2CH_2OH$ | 100–200 | $MSi(OCH_2CH_2O)_3$ |
| 1,2-ethanediol | $Ca(OH)_2$ | $H_2NCH_2CH_2OH$ | 100–200 | $CaSi(OCH_2CH_2O)_3$ |
| 1,2-ethanediol | $Ca(OH)_2$ | $HSCH_2CH_2OH$ | 100–200 | $CaSi(OCH_2CH_2O)_3$ |
| 1,2-ethanediol | $Ca(OH)_2$ | $EtOCH_2CH_2OH$ | 100–200 | $CaSi(OCH_2CH_2O)_3$ |
| 1,2-ethanediol | $Ca(OH)_2$ | $H(OCH_2CH_2)_2OH$ | 100–200 | $CaSi(OCH_2CH_2O)_3$ |
| 1,2-ethanediol | $Ca(OH)_2$ | $HN(CH_2CH_2OH)_2$ | 100–200 | $CaSi(OCH_2CH_2O)_3$ |
| 1,2-ethanediol | $Ca(OH)_2$ | $O(CH_2CH_2OH)_2$ | 100–200 | $CaSi(OCH_2CH_2O)_3$ |
| Pinacol | MOH<br>M = Li, Na, K, Cs | $HOCH_2CH_2OH$ | 100–200 | $M_2Si_2(OCMe_2CMe_2O)_5$ |
| Glycerol | MOH<br>M = Li, Na, K, Cs | $HOCH_2CH_2OH$ | 100–200 | $M_2Si_2(OCH_2CH(CH_2OH)O)_5$ |
| 1,2-propanediol | MOH<br>M = Li, Na, K, Cs | $HOCH_2CH_2OH$ | 100–200 | $M_2Si_2(OCH_2CH(CH_3)O)_5$ |
| 1,3-propanediol | MOH<br>M = Li, Na, K, Cs | $HOCH_2CH_2OH$ | 100–200 | $M_2Si_2(OCH_2CH_2CH_2O)_5$ |
| 1-amino-2,3-propanediol | MOH<br>M = Li, Na, K, Cs | $HOCH_2CH_2OH$ | 100–200 | $M_2Si_2(OCH_2CH(CH_2NH_2)O)_5$ |
| cyclohexane (Cyc) 1,2-diol | $Ca(OH)_2$ | $HOCH_2CH_2OH$ | 100–200 | $CaSi[1,2-(O)_2Cyc]_3$ |
| 1,2-diphenylethane 1,2-diol (dip) | $Ca(OH)_2$ | $HOCH_2CH_2OH$ | 100–200 | $CaSi[1,2-(O)_2Cyc]_3$ |

Additional details on the basic reaction parameters as applied to specific reactants are provided in the Examples section hereinbelow.

After the product is formed in the above reaction, it may either be purified as described above or may be converted in situ into other products, as desired. The silicon or aluminum complexes may be treated with a variety of reactants, including HCl, acetic anhydride, acetyl chloride, additional silica or alumina, and the like. These treatments will produce, in a straightforward manner, various functionalized aluminum- or silicon-containing species. Examples of silicon species that may be obtained in this manner are: $Si(OCH_2CH_2O)_2$, $SiCl_4$, $Si(OAC)_4$, SiC (produced by heating), crystalline silicon species (e.g., quartz), zeolitic-like products, neutral silicon-containing polymers, and the like. Examples of aluminum species are alkali and alkaline earth aluminate glasses and ceramics, etc.

The ionic polymers produced by exchange, e.g., Example 6, can be used as coatable ion conductors for making clear electrodes for electronic displays, nonlinear optical applications and for battery applications.

In addition to the above-described reactions starting with the silicon and aluminum complexes, exchange reactions may also be carried out. In a ligand exchange reaction, the complex is treated with an excess amount of a ligand that is different from the diol used to form the complex. During the reaction, the new ligand will take the place of the originally used diol in the complex.

Alternatively or concurrently, the silicon or aluminum complex may be subjected to a cation exchange reaction by contacting the complex with an excess amount of a cationic species that is different from the starting cationic species. For example, if potassium hydroxide were used in the initial reaction, producing a potassium salt of a penta-coordinate silicon complex, an exchange reaction with an ammonium salt could be used to substitute an ammonium cation for the potassium cation. However, care should be taken in carrying out such a reaction to avoid conditions, particularly acid conditions, in which the cyclic dioxy moiety in the complex is cleaved. Examples of exchange reactions are also described in the Examples section below.

Analogous processes and approaches can be used when $Al_2O_3$ rather than silica is used as the metal oxide reactant.

The invention now being generally described, the same will be better understood by reference to certain specific examples which are included herein for illustrative purposes only, and are not intended to be limiting of the present invention.

EXAMPLES

A. General

1. Procedures. All operations were carried out with the careful exclusion of extraneous moisture. Air-sensitive materials were manipulated using standard Schlenk and glovebox techniques. $^1H$, $^{13}C$ and $^{29}Si$ spectra NMR spectra were taken in $CD_3OD$ and referenced to TMS. All chemicals were purchased from standard vendors and used as received, except the diols, which were distilled under nitrogen before use.

2. Equipment. Infrared spectra were recorded on an IBM FTIR-44 spectro-photometer. Nuclear magnetic resonance data were collected on a Varian 300 MHz spectrometer. Elemental analyses were performed by Galbraith Laboratories in Knoxville, TN.

B. Materials

1. Preparation of $K_2Si_2(OCH_2CH_2O)_5$. 13.8 grams of 400 mesh silica gel (0.23 mol) and 14.8 grams (0.26 mol) of potassium hydroxide (85%) were weighed into a 500 mL round bottom flask. 125 mL of freshly distilled (from $Mg/MgI_2$) EtOH and 250 mL of distilled ethylene glycol were added to the flask and the mixture was heated to boiling. The ethanol fraction was distilled off to remove (by azeotrope) any water formed during the reaction. The mixture was then heated further until the solution appeared homogeneous. Partial dissolution of the silica occurred during this period. Distillation was continued to remove the major fraction of the excess ethylene glycol and water formed during reaction. During distillation, most of the silica dissolved. Upon cooling, the remaining colorless liquid turned to a sticky white solid mass. This mass was taken up in 350 mL of freshly distilled methanol and filtered through a Celite-covered frit. The filtrate was concentrated in vacuo to ~20 mL after which portions of dry acetonitrile were added slowly to precipitate out a fine white powder. The precipitate was then collected on a glass frit and washed with 3×200 mL of acetonitrile. Recrystallization from methanol and acetonitrile/ether resulted in a pure white powder which was vacuum-dried at 130° C. This resulted in 90 g (0.21 mol) of product or 90% yield. NMR: $^1$H, 3.4 ppm (under solvent peak); $^{13}$C, 61.1, 64.3 ppm; $^{29}$Si, −103.0 ppm. Elemental analysis, calc. (found) % C, 27.53 (27.63); % H, 4.98 (4.64); % Si, 13.60 (12.92); % K 17.84 (17.99); % O by difference, 37.01 (36.81).

2. Production of Functionalized Silicon-Containing Species. When $K_2Si_2(OCH_2CH_2O)_5$ is added slowly to neat acetic anhydride and heated, initially, KOAc can be filtered off after the reaction is cooled. Acetyl chloride can also be used. Removal of excess anhydride and 1,2-ethanediacetate under vacuum leads to a white solid which can be characterized as $Si(O_2CCH_3)_4$. Treatment of $K_2Si_2(OCH_2CH_2O)_5$ with two equivalents of HCl, followed by filtration of the KCl leads to the isolation of a neutral tetracoordinate, polymeric silicon compound with the empirical formula $Si(OCH_2CH_2O)_2$, which is in equilibrium with the excess ethylene glycol formed during neutralization to form ring opened diols, e.g., $Si(OCH_2CH_2O)_2(OCH_2CH_2OH)_2$, that can be used in place of $Si(OEt)_4$ for sol-gel processing of silica containing glasses. At higher concentrations, the $Si(OCH_2CH_2O)_2(OCH_2CH_2OH)_2$ species are in equilibrium with oligomeric/polymeric forms whose rheology can be controlled by removal of excess ethylene glycol or solvent addition to form coatable or spinnable materials that can serve as precursors to silicon-containing ceramics. These neutral four coordinate silicon-containing species can be used as precursors to other silicon containing species using techniques common to the polysiloxane synthetic chemist.

3. Preparation of $Li_2Si_2(OCH_2CH_2O)_5$. A procedure similar to that used for the potassium derivative was employed using 5.00 g (0.083 mol) of silica and 1.98 g (0.083 mol) of LiOH. When the "polymeric" portion of the product, that portion which is not immediately soluble, was left stirring for 1-2 days in methanol, it dissolved quantitatively. The resulting methanol-soluble material was recrystallized from methanol and acetonitrile/ether and vacuum-dried at 130° C. This resulted in 26.2 g (71 mmol) of product or 85% yield. $^{13}$C, 61.2, 64.4 ppm; $^{29}$Si, −102.9 ppm.

4. Preparation of $Na_2Si_2(OCH_2CH_2O)_5$. Procedures identical to those described for the preparation of the potassium salt were used except 3.33 g (83 mmol) of NaOH were used. Again, stirring for 1-2 days in methanol resulted in complete dissolution. The methanol-soluble material could be recrystallized as above and dried in vacuum at 130° C. This resulted in 26 g (75 mmol) of product or 90% yield. NMR (CD$_3$OD): $^1$H, 3.36 ppm; $^{13}$C, 63.2 ppm; $^{29}$Si, −103.3 ppm.

5. Preparation of $CsSi(OCH_2CH_2O)_2(OCH_2CH_2OH)$. Procedures identical to those described for the preparation of the potassium salt were used except 8.74 g (83 mmol) of CsOH were used. The product in this instance was entirely soluble in ethanol. The product was precipitated out by addition of acetonitrile. Although almost all of the silica dissolved, the isolated yield (without drying) was only 53%. NMR (CD$_3$OD): $^1$H, 3.4 ppm (under solvent peak); $^{13}$C, 63.2 ppm; $^{29}$Si, −103.1 ppm. Elemental analysis, calc. (found) % C, 20.72 (21.06) % H, 3.63 (3.83); % Si, 8.58 (8.21); % Cs 39.38 (38.84); % O by difference, 27.32 (27.06). IR (nujol) $\nu$ O—H=3000.

6. Exchange of Pinacol for Ethylene Glycol. 1.5 g (3.46 mmol) of $K_2Si_2(OCH_2CH_2O)_5$ were mixed with 80 mL of freshly distilled pinacol (added as a solvent). The reaction mixture was then heated under N$_2$. The mixture melted, the silicate dissolved and heating was continued until 65 mL of a mixture of ethylene glycol and pinacol were distilled off. On cooling, the remaining liquid became a white solid. Excess pinacol was washed away using 2×50 mL of acetonitrile. The remaining white material was then dissolved in methanol and recrystallized as above. The yield was essentially quantitative. The product is expected to be $K_2Si_2(OCMe_2CMe_2O)_5$. NMR (CD$_3$OD): $^1$H, 3.4 ppm (under solvent peak); $^{13}$C, 75.8, 26.5, 25.9 ppm; $^{29}$Si, −109 ppm.

7. Exchange of 1,3-Propanediol for Ethylene Glycol. 5.0 (11.5 mol) of $K_2Si_2(OCH_2CH_2O)_5$ were mixed with 50 mL of freshly distilled 1,3-propanediol (added as a solvent). The reaction mixture was then heated under N$_2$. The silicate dissolved and heating was continued until a 35 mL mixture of ethylene glycol and propanediol was distilled off. The remaining solution was syringed into 50 mL of cold diethyl ether. The product collected as an oil at the bottom of the flask. The oil was cannulated into a 50 mL Schlenk flask and dried in vacuo to a clear glassy solid. This solid was dissolved in 15 mL of MeOH and syringed into 70 mL of acetonitrile to give a precipitate which was filtered off on a medium frit. NMR (CD$_3$OD): $^1$H 1.75 quintet, 1.74 quintet, 3.55 s, 3.66 triplet, 3.67 triplet, 5.13 s ppm; $^{13}$C, 60.0 and 36.3 ppm; $^{29}$Si, −107.2 ppm. The product can be partially polymeric.

8. Exchange of PEG$_4$ for Ethylene Glycol. 5.0 g. (13.5 mmol) of $Li_2Si_2(OCH_2CH_2O)_5$ were mixed with 50 mL of ethylene glycol. The stirred solution was heated under N$_2$ until all of the lithium salt dissolved. 40 mL freshly distilled PEG$_4$ (tetraethylene glycol) were then added. The excess ethylene glycol was distilled off to give a clear yellow solution. 20 mL of PEG$_4$ were removed by distillation at reduced pressure to give a crude glassy polymeric product. The crude material was characterized by $^{13}$C NMR (CD$_3$OD): $^{13}$C, 73.6, 71.3, 64.3 and 62.1. The latter two peaks may indicate that some ethylene glycol remains. The structure may be polymeric.

9. Preparation of $BaSi(OCH_2CH_2O)_3$. 82.5 g BaO and 30.03 g of SiO$_2$ were placed in a 1000 mL flask with 500 mL of ethylene glycol and stirred under N$_2$ for about 1 hour. The BaO and silica slowly dissolved upon continuous distillation under N$_2$. The contents of the flask turned slightly yellowish as the excess ethylene glycol was removed, taking along with it the three moles of water produced as a by-product. The solution also became increasingly viscous. After approximately 350 mL to 400 mL of ethylene glycol had been removed, crystalline material started to form. The contents of the flask were then left to cool overnight, resulting in the formation of a large solid mass. The product was broken up with a spatula and washed with 2×300 mL of acetonitrile, 2×300 mL of absolute ethanol, and finally with 300 mL of acetonitrile. The product was then vacuum dried at approximately 130° C. to obtain approximately 156 g of BaSi(OCH$_2$CH$_2$O)$_3$ as a white, fine flowing powder in a 90% yield by mass. The powder, a monomer, was soluble in methanol.

10. Preparation of CaSi(OCH$_2$CH$_2$O)$_3$. The procedure of Example 9 was repeated using 28.04 g of CaO, 30.04 g of SiO$_2$ and 500 mL of ethylene glycol as starting materials. Approximately 106 g CaSi(OCH$_2$CH$_2$O)$_3$ was obtained as a white, fine flowing powder in an 85% yield by mass. The powder, a monomer, was soluble in methanol.

11. Preparation of MgSi(OCH$_2$CH$_2$O)$_3$. The procedure of Example 9 is followed using MgO as a starting material to obtain MgSi(OCH$_2$CH$_2$O)$_3$ as a white, fine flowing powder in about a 30% yield by mass. The powder, a monomer, was soluble in methanol.

12. Preparation of NiSi(OCH$_2$CH$_2$O)$_3$. BaSi(OCH$_2$CH$_2$O)$_3$ prepared in accordance with Example 9 is dissolved in methanol and mixed with NiSO$_4$ in methanol. Insoluble BaSO$_4$ forms as a precipitate and is separated from the solution. NiSi(OCH$_2$CH$_2$O)$_3$ is recovered from the solution by removal of the solvent.

13. Preparation of CoSi(OCH$_2$CH$_2$O)$_3$. BaSi(OCH$_2$CH$_2$O)$_3$ prepared in accordance with Example 9 is dissolved in methanol and mixed with CoSO$_4$ in methanol. Insoluble BaSO$_4$ forms as a precipitate and is separated from the solution. CoSi(OCH$_2$CH$_2$O)$_3$ is recovered from the solution by removal of the solvent.

14. Synthesis of the aluminum glycolate. 5 g (0.049 mol) of Al$_2$O$_3$ and 7.03 g (0.294 mol) of lithium hydroxide were weighed in a 500 ml round bottom flask. Then 250 ml of ethylene glycol and 60 ml of ethanol were added. The mixture was allowed to heat, and first the ethanol/water azeotrope was distilled off. Then most of the ethylene glycol was removed by distillation. The system was cooled and left under nitrogen overnight; after 12 hours there was a white solid mass, which was treated with methanol; the solid went almost entirely in solution (there was only a slight cloudiness, which was eliminated by filtration through celite). The volume of the solution was reduced under vacuum until a white solid started to precipitate out; the precipitation was completed by adding acetonitrile, and then the product, Li$_3$Al(OCH$_2$CH$_2$O)$_3$, was filtered and dried under vacuum. The yield was quantitative. NMR (CD$_3$OD): $^1$H, 3.58 ppm and 5.11 ppm; $^{13}$C, 64.32 ppm.

15. Preparation of LiAl(OCH$_2$CH$_2$O)$_2$. The procedure of Example 14 is repeated using 2.3 g (0.1 mol) of LiOH as a starting material to obtain a quantitative yield of LiAl(OCH$_2$CH$_2$O)$_2$.

The invention now being fully described, it will be apparent to one of ordinary skill in the art that many changes and modifications can be made thereto, without departing from the spirit or scope of the invention as set forth herein.

The embodiments of the invention in which an exclusive property or privilege is claimed are defined as follows:

1. A complex having the formula I or II:

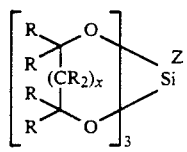
I

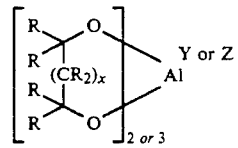
II wherein x is 0 or 1; each R is independently selected from the group consisting of H, OH, C$_{1-6}$ alkyl, C$_{1-6}$ alkoxy, C$_{2-6}$ alkene, C$_{6-12}$ aryl, C$_{1-6}$ hydroxyalkyl, C$_{1-6}$ thioalkyl, C$_{2-12}$ alkoxyalkyl, C$_{3-20}$ heteroaromatic, and combinations thereof, and wherein each said R group may further contain one or more atoms of elements selected from the group consisting of Si, Ge, Sn and P; Y is a monovalent cation and Z is a multivalent cation.

2. A complex according to claim 1, wherein each R is independently a methyl group or H.

3. A complex according to claim 1, wherein each R is H.

4. An complex according to claim 1, wherein Y is an alkali metal cation.

5. A complex according to claim 1, wherein Z is an alkaline earth metal cation.

6. A complex according to claim 1, wherein Y is Na$^+$, K$^+$, Li$^+$ or Cs$^+$.

7. A complex according to claim 1, wherein Z is Mg$^{2+}$, Ca$^{2+}$, Ba$^{2+}$, Ni$^{2+}$ or Co$^{2+}$.

8. A silicon complex selected from the group consisting of MgSi(OCH$_2$CH$_2$O)$_3$, CaSi(OCH$_2$CH$_2$O)$_3$, BaSi(OCH$_2$CH$_2$O)$_3$, NiSi(OCH$_2$CH$_2$O)$_3$, and CoSi(OCH$_2$CH$_2$O)$_3$.

9. A method of producing a silicon or aluminum complex, which comprises: reacting silica or alumina with a compound having the formula:

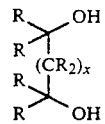

wherein x is 0 or 1; each R is independently selected from the group consisting of H, OH, C$_{1-6}$ alkyl, C$_{1-6}$ alkoxy, C$_{2-6}$ alkene, C$_{6-12}$ aryl, C$_{1-6}$ hydroxyalkyl, C$_{1-6}$ thioalkyl, C$_{2-12}$ alkoxyalkyl, C$_{3-20}$ heteroaromatic, and combinations thereof in the presence of a base and with removal of water formed during the reaction to produce a silicon or aluminum complex, and recovering the complex, with the proviso that when the complex is a silicon complex, the base comprises a mutivalent cationic species.

10. A method according to claim 9, wherein said reaction is conducted at a temperature of from about 20° C. to about 200° C.

11. A method according to claim 9, wherein said water is removed by distillation.

12. A method according to claim 11, wherein said water is removed by azeotropic distillation.

13. A method according to claim 9, wherein the complex produced in said reaction is recovered by filtration followed by crystallization.

14. A method of claim 9, wherein said water is removed by reaction with water scavenger.

15. A method of claim 9, wherein said water is removed by membrane transport.

16. A method of claim 9, wherein said complex has the formula I or II:
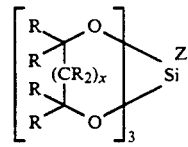
I
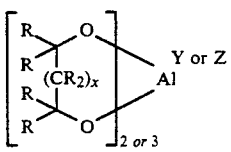
II
wherein x is 0 or 1; each R is independently selected from the group consisting of H, OH, $C_{1-6}$ alkyl, $C_{1-6}$ alkoxy, $C_{2-6}$ alkene, $C_{6-12}$ aryl, $C_{1-6}$ hydroxyalkyl, $C_{1-6}$ thioalkyl, $C_{2-12}$ alkoxyalkyl, $C_{3-20}$ heteroaromatic, and combinations thereof; Y is a monovalent cation and Z is a multivalent cation.
* * * * *

UNITED STATES PATENT AND TRADEMARK OFFICE
CERTIFICATE OF CORRECTION

PATENT NO. : 5,216,155
DATED : June 1, 1993
INVENTOR(S) : R. M. Laine et al.

It is certified that error appears in the above-identified patent and that said Letters Patent is hereby corrected as shown below:

| COLUMN | LINE | | |
|---|---|---|---|
| 4 | 41 & 42 | "pro-cess" should read --processes-- | |
| 6 | 41 | "bse" should read --base-- | |
| 7 | 20 | "-HOCH$_2$C$_2$OH" should read -- -HOCH$_2$CH$_2$OH-- | |
| 8 | 33 | "crystaline" should read --crystalline-- | |
| 11 | 42 | after "silicon" insert --containing-- | |
| 14 | 23 | "5.0" should read --5.0 g-- | |
| 14 | 35 & 36 | "3.55 s" should read --3.35 s-- | |

Signed and Sealed this

Fourth Day of January, 1994

*Attest:*

BRUCE LEHMAN

*Attesting Officer*      *Commissioner of Patents and Trademarks*